United States Patent [19]

Gauneus et al.

[11] Patent Number: 4,888,019
[45] Date of Patent: Dec. 19, 1989

[54] ARTICULAR PROSTHESIS AND ITS PREPARATION PROCESS

[75] Inventors: Gilbert Gauneus, Meudon; Maryvonne Nicaise, Orsay; Kifu O. Tran, Les Ulis, all of France

[73] Assignee: Compagnie Oris Industrie S.A., Paris, France

[21] Appl. No.: 419,002

[22] Filed: Sep. 9, 1982

[51] Int. Cl.$^4$ .................................................. A61F 2/30
[52] U.S. Cl. ......................................................... 623/18
[58] Field of Search ..................... 525/276; 623/16, 18, 623/20, 22, 23, 1

[56] References Cited

U.S. PATENT DOCUMENTS

| 3,676,190 | 7/1972 | Landler | 525/276 |
|---|---|---|---|
| 3,933,773 | 1/1976 | Fuerster | 525/276 |
| 4,031,167 | 6/1977 | Aronolf et al. | 525/276 |
| 4,113,912 | 9/1978 | Okita | 428/422 |
| 4,208,472 | 6/1980 | Cho et al. | 428/422 |
| 4,377,010 | 3/1983 | Fydelor et al. | 128/92 C |

FOREIGN PATENT DOCUMENTS

| 1122634 | 9/1956 | France | 128/92 C |
|---|---|---|---|
| 7301728 | 2/1973 | Netherlands | 623/18 |

*Primary Examiner*—Richard J. Apley
*Assistant Examiner*—David J. Isabella
*Attorney, Agent, or Firm*—James E. Nilles

[57] ABSTRACT

A polymer articular prosthesis having a sliding surface, wherein the latter is constituted by a thin layer of said polymer grafted with tetrafluoro-ethylene.

The process for preparing the articular prosthesis comprises coating with a protective varnish the outer surface of a polymer articular prosthesis having a sliding surface, except in the areas constituting this sliding surface irradiating the prosthesis with ionizing rays, contacting the prosthesis with the tetrafluoroethylene vapour for adequate time to bring about tetrafluoroethylene grafting over a limited thickness of the polymer forming the sliding surface and then removing the protective varnish.

6 Claims, 3 Drawing Sheets

ARTICULAR PROSTHESIS AND ITS PREPARATION PROCESS

BACKGROUND OF THE INVENTION

The present invention relates to an improved polymor articular prosthesis and to its preparation process. More specifically, it relates to a total or partial articular prosthesis, whose properties have been improved both with respect to the friction coefficients of its sliding surface and with respect to its resistance to deformation.

For some years now, the problems caused by the treatment of patients such as those suffering from arthrosis of the hip have been solved by surgical operations consisting of removing the attached parts of the joint and replacing them by metallic, ceramic or plastic prostheses in order to obtain friction coefficients compatible with a satisfactory operation of the joint.

The human joint has in fact a particularly low friction coefficient and the specific properties of the synovia and the cartilage enable the joint to respond to the needs resulting from long-term frictional work under stress.

When it is necessary to use articular prostheses, it is not the intention to replace all the mechanisms controlling a healthy joint, but solely to fit new articular surfaces, whilst then assisting the adaptation to the prosthesis of the neuromuscular control, the ligament system, the capsule and the synovia, every effort being made to preserve their functions.

In order to facilitate this adaptation, the prostheses are made so as to be able to reproduce as faithfully as possible the natural shapes and the geometry of the joint. Moreover, the choice of the materials used for the prosthesis is very important, in view of the sliding properties which it must have and the forces exerted on the hinge points constituted by the joints. Thus, the articular sliding surfaces must have an easy friction, but must not wear to an exaggerated extent, because it is necessary to prevent the formation of wear debris or fragments which, as a function of their grain size, could lead to inflammation.

Hitherto, articular prostheses have been made from metal, ceramics or plastics.

Metallic prostheses have the disadvantage of leading to the formation of wear debris, which is very unsatisfactorily tolerated when the sliding surfaces of the joint are both made from metal. Metallic prostheses have in any case been largely abandoned, due to their defects.

Ceramic prostheses have the advantage of very low friction coefficients when used either in direct contact with the healthy part of a joint, or in contact with a polyethylene or ceramic part. However, they have the disadvantage of being fragile and brittle, which leads to in vitro breaking accidents.

Plastic prostheses are generally used in contact with a metallic part, which makes it possible to obtain a very low friction coefficient of the joint. The metal is either a chromium - cobalt alloy, or stainless steel and the plastic prosthesis is generally made from high density polyethylene. However, these articular prostheses have the disadvantage of leading to the formation of relatively well tolerated, but unacceptable wear debris, whilst suffering from deformations due to creep, which are prejudicial to the satisfactory functioning of the prosthesis.

BRIEF SUMMARY OF THE INVENTION

The present invention relates to an improved articular prosthesis made from polymerized plastic, which obviates the aforementioned disadvantages.

To this end, the polymerarticular prosthesis comprises a sliding surface, which is made from a thin layer of said polymer grafted with tetrafluoroethylene.

As a result of the thin tetrafluoroethylenegrafted polymer layer, the friction coefficient of the prosthesis is improved, whilst retaining the interesting mechanical properties of the polymer from which it is made.

The process used leads to a local modification of the polyethylene by grafting C2 F4 and to the formation of an ethylene - tetrafluoroethylene copolymer, which makes it possible to improve the friction characteristics and provides better creep resistance. Thus, the simultaneously applied crosslinking prevents the irreversible sliding of the copolymer chains observed in the case of pure polytetrafluoroethylene which, under the action of radiation, degrades and does not crosslink. Thus, the mobility of the polymer chains increased by the presence of fluorine-containing elements does not lead to creep and instead facilitates the return of the copolymer to its initial structure.

Crosslinked ethylene - polytetrafluoroethylene copolymer

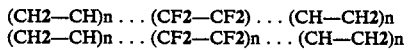

Non-crosslinked polytetrafluoroethylene polymer

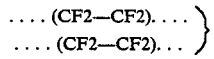

In general, the thickness of the grafted polymer layer is approximately 0.3 to 0.5 $\mu$m.

According to a preferred embodiment of the invention, the prosthesis is made from a crosslinked polymer, which leads to a further improvement of its mechanical properties. In this case, it advantageously comprises a part constituted by polymer crosslinked to a higher degree than the remainder of the prosthesis. The location of the more highly crosslinked part is chosen as a function of the mechanical stresses undergone by the prosthesis in order to correspond to the location where the compressive stresses are highest.

Thus, the creep resistance of the prosthesis is improved by creating an area of grater hardness at the point where the stresses are highest. As a result of the special prosthesis structure according to the invention, i.e. the presence of areas of polymer crosslinked to different degrees and a sliding surface formed from tetrafluoroethylene-grafted polymer, it is possible to obtain appropriate hardnesses and in particular avoid having excessive hardness on the sliding surface, which would lead to the formation of abrasive debris causing greater wear.

In order to obtain good friction coefficients, it is advantageous for the degree of tetrafluoroethylene grafting of the layer of limited thickness forming the sliding surface to be 0.3 to 2.5 mg of tetrafluoroethylene per cm$^2$ of surface.

It is pointed that this degree of grafting corresponds to the formula $P_m/s$ in which $P_m$ represents the weight quantity of tetrafluoroethylene in the prosthesis and s represents the outer surface of the grafted polymer layer constituting the sliding surface.

According to the invention, the polymer constituting the prosthesis can be chosen from the group including polyolefins such as polyethylene and polypropylene, polystyrene, polyacrylates, polyvinylchloride, polyamides and polyesters.

The choice of polymer depends more particularly on the joint which the prosthesis is to replace and is made whilst taking account of the mechanical properties of the polymer is order to obtain the desired mechanical characteristics of the joint to be replaced (knee, shoulder, ankle, fingers, etc). Preferably and in particular in the case of the hip prosthesis, the polymer is polyethylene.

The invention also relates to a process for the preparation of a prosthesis having the aforementioned characteristics and which comprises:

(a) coating with a protective varnish, which is impermeable are inert with respect to tetrafluoroethylene, the outer surface of a polymer articular prosthesis having a sliding surface except in the area or areas forming the said sliding surface, (b) irradiating with ionizing rays the thus coated prosthesis, (c) bringing the thus irradiated prosthesis into contact with tetrafluoroethylene vapour for an adequate period to bring about tetrafluoroethylene grafting on a limited thickness of the polymer forming the sliding surface, and (d) eliminating the protective varnish.

When working in this way and carrying out irradiation under appropriate conditions, it is possible to obtain on the one hand a crosslinking of the polymer constituting the prosthesis and on the other the grafting of the tetrafluoroethylene solely on that surface of the prosthesis which is not protected by the varnish.

The varnish serves merely to protect the prosthesis, i.e. to render it waterproof in order to prevent any contact with the monomer in the vapour state and consequently prevent the grafting of the monomer to the areas of the prosthesis which are protected.

This varnish must be impermeable and inert to tetrafluoroethylene, have a good wettability with respect to the polymer, have a good stability, have a limited susceptibility to tearing, remain flexible and have an adequate resistance to ionizing radiation. Moreover, it must have an adequate adhesion in order to effectively protect the prosthesis and must be easy to eliminate then at the end of the operation, preferably by detaching it.

Finally, it is preferable that it retains its 30 mechanical properties at low temperatures, e.g. at $-100°$ C. Thus, in order to bring the coated prosthesis into contact with the gaseous monomer, there is generally a transfer of the gaseous monomer by cooling the container in which the prosthesis elements to be grafted are located.

As varnishes which can be used, reference is made to the varnishes based on vinyl resins, such as the product marketed under the trade name Nucletex and which corresponds to the following formulation:

| | |
|---|---|
| vinylite resin VYHH (87% vinyl chloride, 13% vinyl acetate) | 8 parts by weight |
| vinylite resin VYNS (90% vinyl chloride, 10% vinyl acetate) | 18 parts by weight |
| paraflex (polyester) | 8 parts by weight |
| dioctyl phthalate | 6 parts by weight |
| solvent (methyl ethyl ketone) until dissolved. | |

This varnish is applied to the prosthesis by conventional processes, e.g. by means of a brush. After drying, the thus protected prosthesis is irradiated with ionizing radiation, which leads both to the crosslinking of the polymer and to the production of free radicals forming the active sites for the grafting. This radiation is carried out in the absence of oxygen, e.g. under vacuum or in an inert gas atmosphere, e.g. a nitrogen atmosphere. The ionizing radiation which can be used are Y rays, ultraviolet rays or electron beams. Preferably, the irradiation is carried out by means of an electron beam having an energy of 2.5 to 3 MeV with a dose of 10 to 15 Mrad.

After irradiation, the prosthesis is brought into contact with the tetrafluoroethylene vapour in order to graft it to the polymer in the prosthesis area or areas not protected by the varnish. This contacting operation is carried out at a temperature and for a time chosen as a function of the degree of grafting which it is desired to obtain. This degree of grafting can be controlled by acting on the energy and irradiation dose applied, on the pressure of the monomer, on the temperature and on the contact time with the monomer.

In order to obtain a degree of grafting of 0.3 to 2.5 mg/cm$^2$, the prosthesis is contacted with the tetrafluoroethylene for 50 to 70 hours at a tetrafluoroethylene pressure of 1.2 to 1.6 bar.

The degree of crosslinking of the polymer forming the prosthesis can be regulated by acting on the energy of the ionizing radiation beam, on the irradiation dose and on the orientation of the prosthesis with respect to the beam.

According to a variant of the process according to the invention, the irradiation of the prosthesis is carried out in two stages, in order to bring about in the first stage the crosslinking of the polymer forming the prosthesis and in order to bring about in the second stage the pre-irradiation necessary for grafting.

In this case, after applying the varnish to the parts of the prosthesis to be protected, the first stage is preferably carried out by means of λ radiation and the second stage by means of an electron beam.

However, it is possible to apply the varnish between the two irradiation stages in which case the process comprises:

(a) irradiating a polymer articular prosthesis having a sliding surface by means of ionizing radiation in order to crosslink the polymer, (b) coating with a protective varnish which is impermeable and inert with respect to tetrafluoroethylene the outer surface of the crosslinked polymer articular prosthesis, with the exception of the area or areas forming the sliding surface, (c) irradiating the thus protected prosthesis by means of ionizing rays, (d) bringing the thus irradiated prosthesis into contact with the tetrafluoroethylene vapour for a period adequate to obtain the grafting of the tetrafluoroethylene to a limited thickness of the polymer forming the sliding surface, and (e) eliminating the protective varnish.

In the same way as indicated hereinbefore, the crosslinking stage is preferably carried out by irradiating then with λ rays, whilst the irradiation stage of the varnish-protected prosthesis is carried out by means of an electron beam.

In order to obtain in the prosthesis a part formed from crosslinked polymer having a higher degree of crosslinking than the remainder of the prosthesis, it is possible to use conventional processes, e.g. choosing the energy of the radiation treatment so as to obtain different degrees of crosslinking. Preferably, in order to achieve this result, the irradiation is carried out in such a way that the prosthesis receives the ionizing radiation under two different orientations.

In this case, the irradiation of the prosthesis can be carried out in two stages and the prosthesis position relative to the radiation beam can be modified between the two stages, in such a way that one area of the prosthesis receives two irradiation doses, whilst the remainder thereof only receives a single irradiation dose. Thus, a higher degree of crosslinking is obtained in the area having received two doses. The position of this area is chosen in such a way that it corresponds to the orientation axis of the joint supporting the highest pressures and stresses.

BRIEF DESCRIPTION OF THE DRAWINGS.

The invention is described in greater detail hereinafter relative to non-limitative examples and the attached drawing, wherein show.

EXAMPLE 1

This example relates to the treatment of a polyethylene hip prosthesis, whose shape corresponds to the part of the hip bone including the cotyloid.

Firstly, a varnish constituted by the product Nucletex is applied by means of a brush to the outer surface of the prosthesis, except the inner cavity of the cotyloid. The thus coated prosthesis then undergoes λ irradiation in vacuo by means of a cobalt 60 source under the following conditions:
dose rate: 0.27 Mrad/h
dose: 15 Mrad.

The prosthesis then undergoes a further irradiation in vacuo by means of an electron beam having an energy of 3 MeV, a beam intensity of 400 μA and a dose of 13 Mrad. Following irradiation, tetrafluoroethylene is introduced into the vacuum enclosure containing the prosthesis at a pressure of 1.5 bar and a temperature of 15° C. and the prosthesis is left in contact with the tetrafluoroethylene for 50 hours, which makes it possible to graft the tetrafluoroethylene to the unprotected parts of the prosthesis. Following this grafting stage, the protective varnish coating is removed by disengaging it from the prosthesis. The degree of grafting is then determined and this corresponds to formula $P_{ms}$ with $p_m = p_f - p_i$ in which $p_f$ represent the weight of the prosthesis after grafting, $P_i$ the weight of the prosthesis before grafting and S the surface of the prosthesis not protected by the varnish. Under these conditions, the degree of grafting obtained is 0.318 mg of tetrafluoroethylene per cm$^2$ of unprotected surface.

Figure 1:
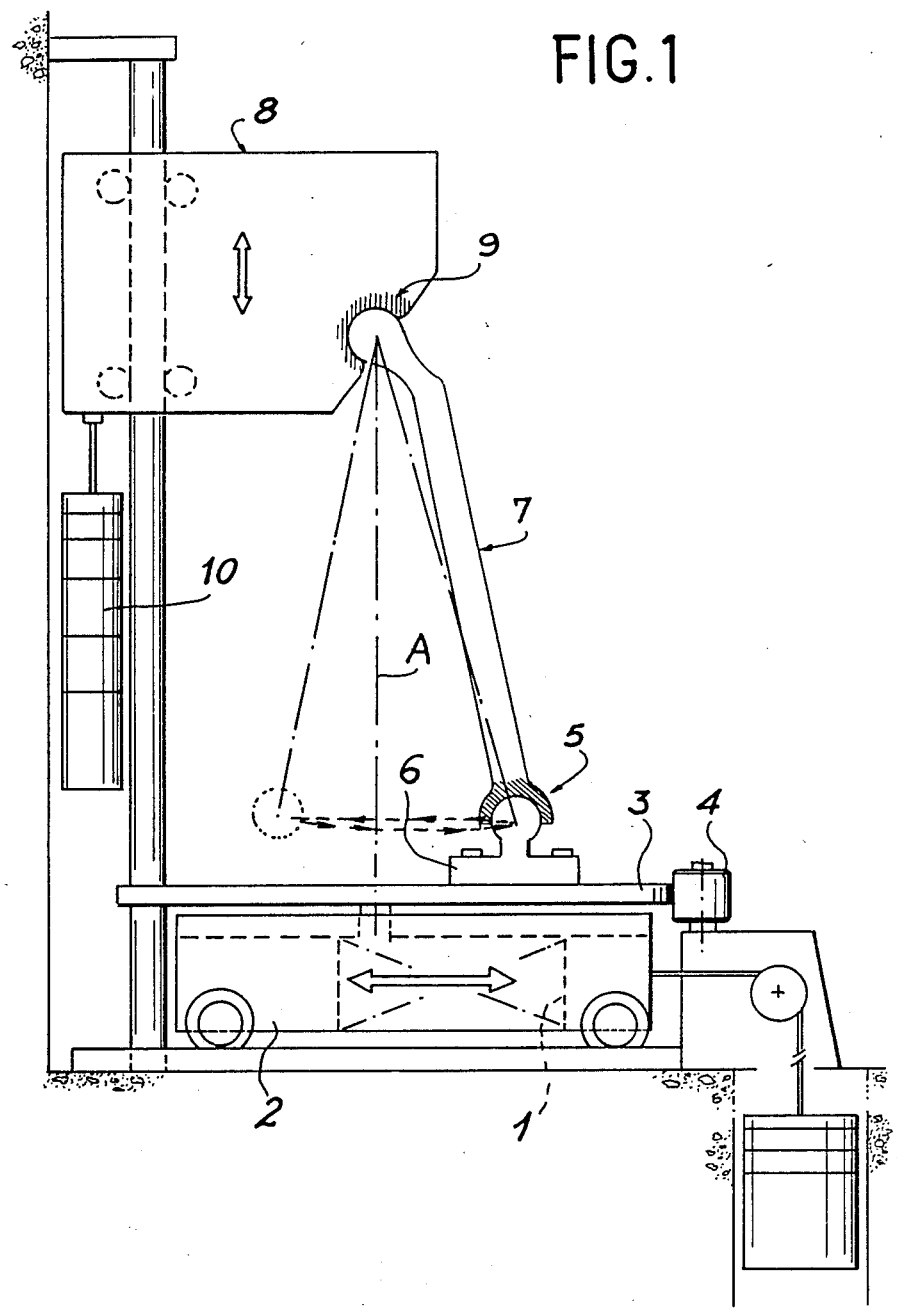
FIG. 1 the device used for testing the deformation resistance of articular prostheses according to the invention.

The thus obtained prosthesis then undergoes wear test carried out by means of the device shown in FIG. 1. This device comprises a geared motor 1, to which is vertically fixed a trolley 2 moving in accordance with and axis 3, a cam 3 integral with the geared motor 1 and in permanent contact with a fixed roller 4, a crank means 6 driven by the geared motor 1 and on which is installed a cardan joint 5 receiving the base of a femur 7, a second trolley 8 perpendicular to the first and moving in a vertical plane supporting the prosthesis 9 to be tested and the load 10. The device also comprises a distilled water supply, used for lubricating the parts in friction.

Figure 2:
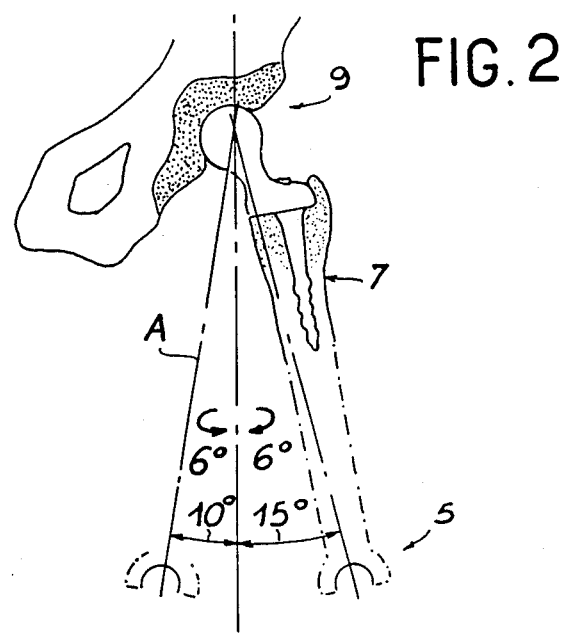
FIGS. 2 and 3 the kinematics of the test device.

In operation, the geared motor 1 drives the crank 6, whose circular movement is deteriorated by cam 3 in contact with roller 4, so that the circular movement of crank 6 is accompanied by an alternating displacement of the centre of rotation of the crank in the action plane of the trolley. Therefore, the displacement of the crank is modified and approximately assumes an elliptical shape and the length difference between the major axis and the minor axis of the ellipse produces, at the head of the femur, two displacements of the vertical trolley 8 supporting prosthesis 9. One revolution of cam 3 ensuring the displacement of femur 7 and prosthesis 9 corresponds to one cycle. FIG. 2 shows the movement described by the head of the femur in the cotyloid of prosthesis 9 during one cycle. This movement is broken down in the manner indicated hereinafter.

Figure 3:
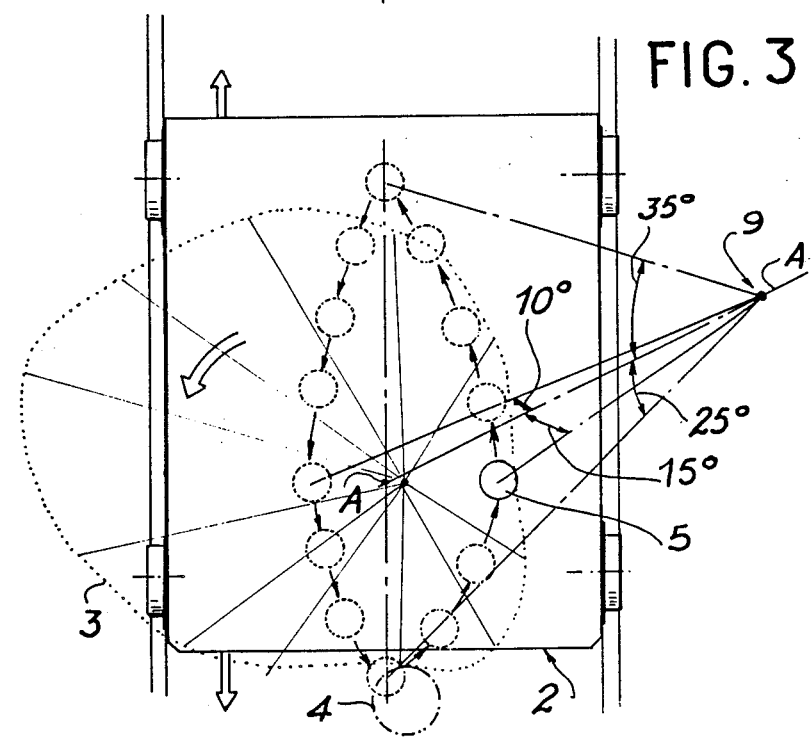

An angular displacement of the femur 7 from the back to the front is obtained by describing, relative to the vertical and in the walking direction, firstly an angle of 25° and then an angle of 35°, the limit between these two angles being the vertical plane perpendicular to the step in which passes the axis of symmetry A of the skeleton. This lateral displacement towards the outside is accompanied by a displacement by a maximum angular value of 15° in the same vertical plane. To return to the initial position, there is an inward lateral displacement of 10°. In addition to the two movements described hereinbefore, during one cycle, the femur pivots coaxially at the diaphysis by an angle of ±6°. All the alternating and rotary movements described hereinbefore during a cycle at the knee, determines the asymmetrical figure shown in FIG. 3, whose limits are a function of the allowed angular displacements.

This arrangement ensures a total scan of the cotyloid by the head of the femur under conditions very similar to those encountered in vivo for the most frequently encountered positions of the lower member at the knee (forward movement, backward movement, direction change, etc).

For the purpose of the present tests, the load 10 applied to the mobile means supporting the prosthesis is 100 daN and the geared motor is operated at a speed of 25 cycles per minute. At the end of 500,000 cycles, the profile of the cotyloid is examined and its geometry is compared with that of an untreated polyethylene cotyloid.

The results obtained are illustrated in FIG. 4 which shows the deformations observed on the cotyloid treated by the process of the invention (4a, 4b, 4c, 4d) and the deformations observed on an identical untreated cotyloid (4c).

FIGS. 4a, 4b, 4c, 4d are sections of the cotyloid respectively in accordance with planes perpendicular to the base of the hemisphere defined by the inner cavity of the cotyloid and passing through the centre of said hemisphere, said planes being displaced by 45° relative to one another.

Figure 4A:
FIG. 4 deformations observed on the cotyloid of the prosthesis of example 1.
Figure 4B:
Figure 4C:
Figure 4D:
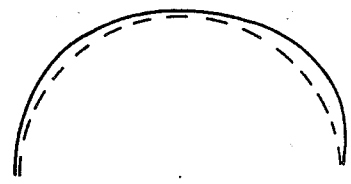
Figure 4E:

It is apparent that the cotyloid treated by the process of the invention has few deformations compared with the untreated cotyloid, whose section is made in accordance with the same plane as that of FIG. 4a.

EXAMPLE 2

A polyethylene prosthesis identical to that of example 1 is used and the same varnish is applied to its outer surface, with the exception of the inner cavity of the cotyloid. The thus coated prosthesis undergoes irradiation in vacuo by means of an electron beam with an energy of 3 MeV, a beam intensity of 400 µA and a dose of 13 Mrad, by orienting the prosthesis in such a way that the beam is perpendicular to the concavity of the spherical part.

The irradiated prosthesis is then brought into contact with the tetrafluoroethylene under a pressure of 1.5 bar, at a temperature of 15° C. and for 50 hours. Under these conditions, the degree of grafting is 0.462 mg of tetrafluoroethylene per $cm^2$.

The thus treated prosthesis is subject to the wear tests performed under the same conditions as in example 1. The results obtained are given in FIG. 5.

Figure 5A:
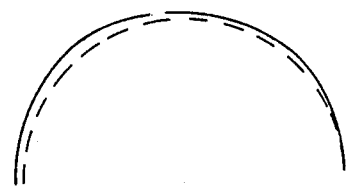
FIG. 5 the deformations observed on the cotyloid of the prosthesis of example 2.
Figure 5B:
Figure 5C:
Figure 5D:
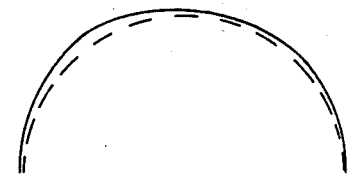
Figure 5E:
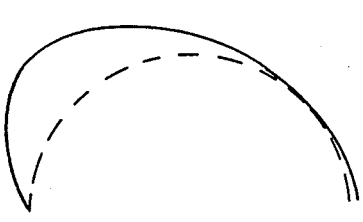

In FIG. 5, references 5a, 5b, 5c and 5d relate to sections made under the same conditions as sections 4a, 4b, 4c and 4d of FIG. 4 and 5e relates to a section of an untreated cotyloid made in the same plane as section 5a.

It is apparent that the deformations of the treated cotyloid are much less pronounced than those of the untreated cotyloid. Furthermore, compared with the prosthesis obtained in example 1, the results are better, the deformations being less pronounced and more regular with respect to the centre of the cavity.

It would seem that in the case of example 1 where the crosslinking is performed by irradiation before grafting, a higher crosslinking of the polymer is obtained and consequently a lower degree of tetrafluoroethylene grafting, because the tetrafluoroethylene penetrating the polymer by diffusion does so less well as a result of the crosslinking.

In addition, due to the higher degree of crosslinking and the lower degree of grafting, the hardness of the prosthesis sliding surface is higher and the debris formed doubtless too abrasive, which leads to higher wear to the prosthesis.

EXAMPLE 3

This example relates to the grafting of the sliding surface of a polyethylene prosthesis identical to that of example 1.

Crosslinking and grafting are carried out simultaneously by using the experimental irradiation conditions of example 2 after protecting the outer surface of the prosthesis, with the exception of the inner cavity of the cotyloid, by means of the same protective varnish as in example 1.

Following irradiation, the prosthesis is brought into contact with the tetrafluoroethylene at a pressure of 1.5 bar, a temperature of 15° C. and a time of 65 hours, followed by the removal of the varnish. Under these conditions, the degree of grafting obtained is 1.32 mg of tetrafluoroethylene per $cm^2$. The thus obtained prosthesis undergoes an examination by electron spectroscopy, which makes it possible to locate the fluorine atoms. This reveals that these atoms are located at a depth up to 3000 Å, which shows that the grafting has taken place on a polymer layer of limited thickness.

EXAMPLE 4

A polyethylene prosthesis identical to that of example 1 is used and it undergoes the coating and irradiation operations under the same conditions as in example 2.

After irradiation the prosthesis is brought into contact with the tetrafluoroethylene at a pressure of 1.5 bar, a temperature of 20° C. and a time of 65 hours. The degree of grafting obtained is 2 mg of tetrafluoroethylene per $cm^2$. The prosthesis is then examined by electron spectroscopy to locate the fluorine atoms. In this case, the fluorine atoms are at a depth of 5000 Å. Thus, this grafting method makes it possible to graft the tetrafluoroethylene over a limited thickness of the unprotected surface of the prosthesis.

What is claimed is:

1. A polymeric articular prosthesis having a sliding surface, wherein the prosthesis comprises a polymer and the sliding surface comprises a thin layer of a graft copolymer of polytetrafluoroethylene and said polymer, wherein said graft copolymer is obtained by grafting tetrafluoroethylene onto said polymer at said sliding surface so that the degree of tetrafluoroethylene grafting of the thin layer forming the sliding surface is 0.3 to 2.5 mg of tetrafluoroethylene per $cm^2$ of surface.

2. A polymeric articular prosthesis having a sliding surface, wherein said prosthesis is made of a polymer and said sliding surface consists essentially of a thin layer of a graft copolymer of polytetrafluoroethylene and said polymer, wherein said sliding surface of graft copolymer is obtained by grafting tetrafluoroethylene onto said polymer at said sliding surface so that the degree of tetrafluoroethylene grafting of the thin layer forming the sliding surface is 0.3 to 2.5 mg of tetrafluoroethylene per $cm^2$ of surface.

3. The prosthesis according to claim 2, wherein the polymer forming the prosthesis is crosslinked.

4. The prosthesis according to claim 3, wherein in a portion of the prosthesis other than the sliding surface, the polymer is crosslinked at a higher degree than in the remainder of the prosthesis.

5. The prosthesis according to claim 1 or 2, wherein the polymer is selected from the group consisting of polyolefins, polystyrene, polyacrylates, polyvinylchloride, polyamides and polyesters.

6. The prosthesis according to claim 1 or 2, wherein the polymer is polyethylene.

* * * * *

UNITED STATES PATENT OFFICE
CERTIFICATE OF CORRECTION

Patent No. 4,888,019        Dated December 19, 1989

Inventor(s) Gilbert Gaussens, Maryvonne Nicaise, Kieu Oanh Tran

It is certified that error appears in the above-identified patent and that said Letters Patent is hereby corrected as shown below:

On the face page, line (75), correct the spelling of the first inventor's name to -- Gilbert Gaussens --; and the second inventor's name to -- Kieu O. Tran --.

Signed and Sealed this

Sixteenth Day of October, 1990

*Attest:*

HARRY F. MANBECK, JR.

*Attesting Officer*      *Commissioner of Patents and Trademarks*